United States Patent [19]

Reynaud

[11] 4,331,188
[45] May 25, 1982

[54] APPARATUS FOR TRANSFERRING A PASTY MATTER FOR FILLING A HOLLOW BODY

[76] Inventor: Marc Reynaud, 29 B Agutte Semhat, 38000 Grenoble, France

[21] Appl. No.: 105,158

[22] Filed: Dec. 19, 1979

[51] Int. Cl.³ ................................................ B65B 3/04
[52] U.S. Cl. ............................... 141/311 R; 141/392; 60/577; 222/179.5; 222/386; 222/387
[58] Field of Search ........................ 141/1–12, 141/311 R, 392; 222/179.5, 386, 387; 60/576, 577, 578; 92/51, 52, 66

[56] References Cited

U.S. PATENT DOCUMENTS

| | | | |
|---|---|---|---|
| 3,331,538 | 7/1967 | Higgins | 222/387 |
| 3,975,239 | 8/1976 | Stamer | 141/1 |

*Primary Examiner*—Houston S. Bell, Jr.
*Attorney, Agent, or Firm*—McAulay, Fields, Fisher, Goldstein & Nissen

[57] ABSTRACT

The present invention relates to an apparatus for transferring a pasty matter for filling a hollow body.

This apparatus comprises a cylindrical bowl in which the pasty matter to be transferred is placed and of which the bottom is extended by an axial tube open at its two ends, a push member being engageable in the bowl to push the pasty matter towards and in the axial tube, this push member having an outer diameter substantially equal to the inner diameter of the bowl and having an axial bore passing therethrough and a piston constituted by a rod of diameter equal to the inner diameter of the axial tube extending the bowl, housed and slidable in the axial bore of the push member to be engaged in the axial tube of the bowl and empty this tube of the pasty matter that it contains.

6 Claims, 6 Drawing Figures

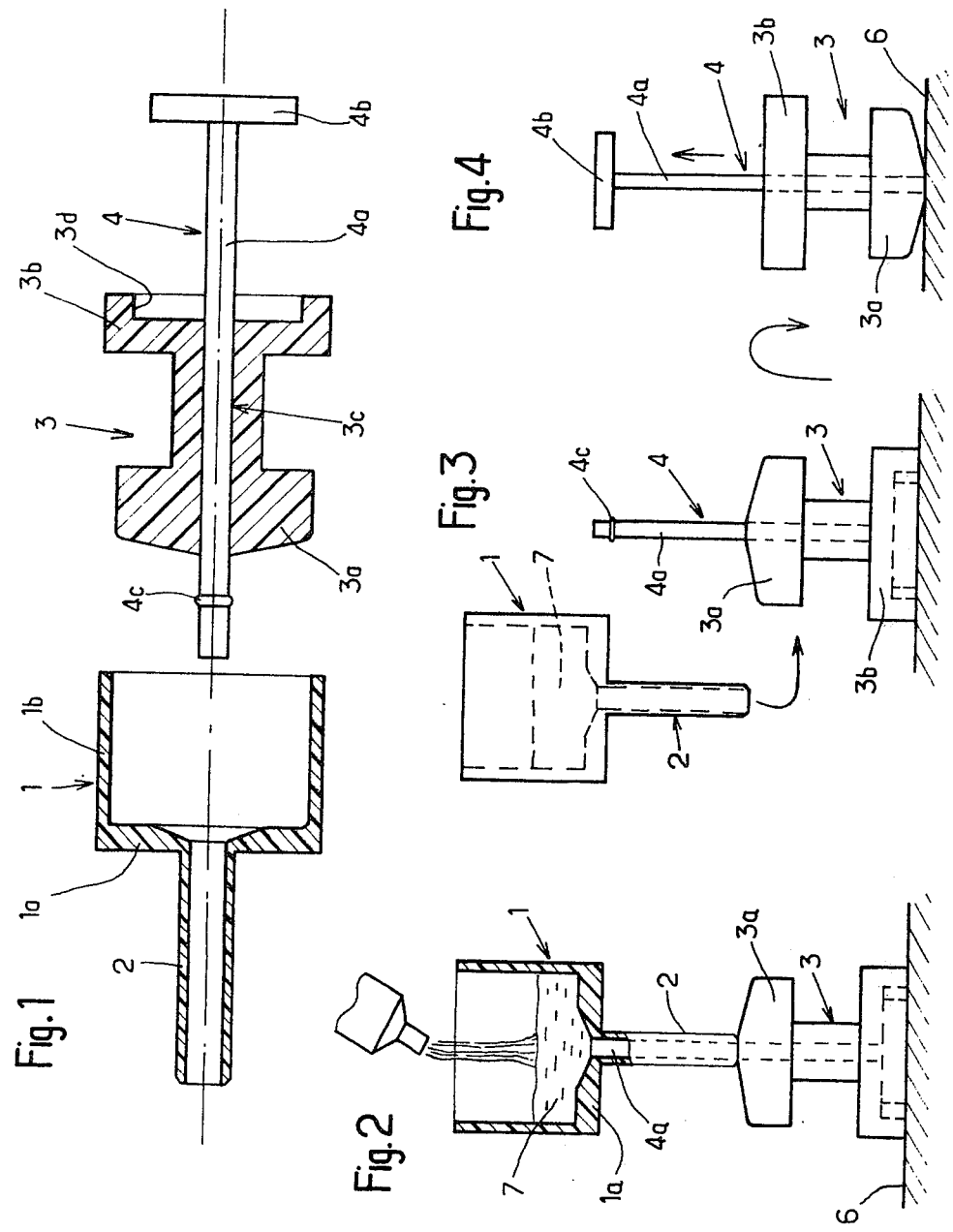

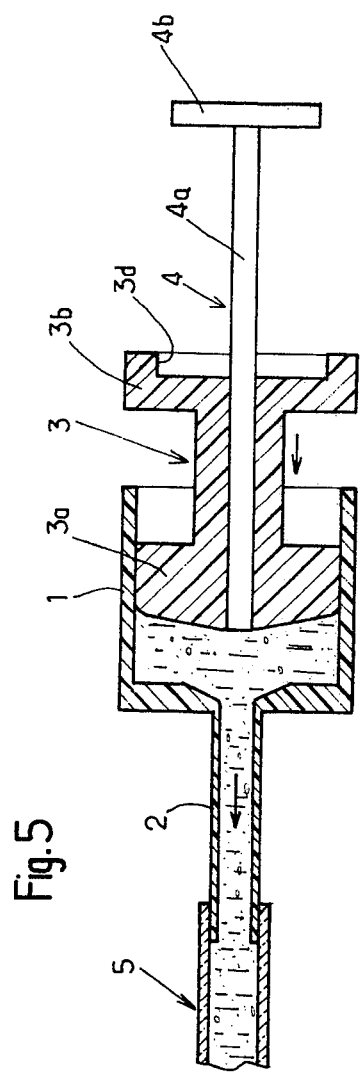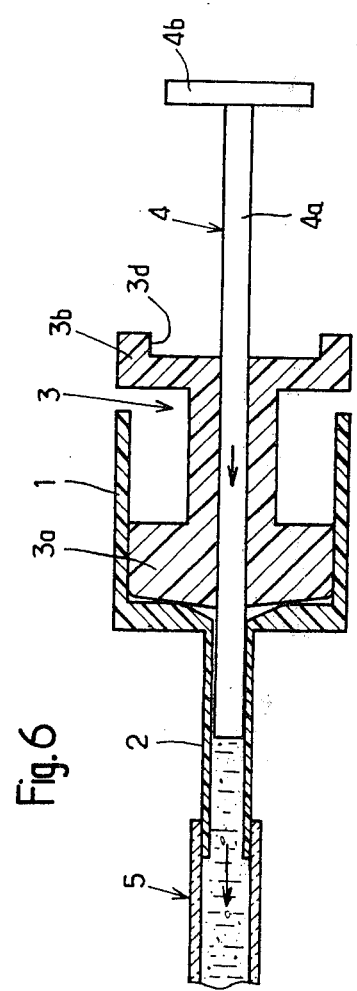

APPARATUS FOR TRANSFERRING A PASTY MATTER FOR FILLING A HOLLOW BODY

BACKGROUND OF THE INVENTION

The present invention relates to an apparatus for transferring a pastry matter for filling a hollow body, such as a syringe body used for the injection, under pressure, of a dental impression.

To fill the body of a syringe for injecting an impression material, a bowl or a glass plate was heretofore used, on which a mixture of silicone and catalyst was made. The syringe was then filled, more or less well, with the formation of numerous air bubbles and a considerable loss of silicone. In addition, this filling took much time, which is prejudicial as the silicone begins to set as soon as the catalyst is received.

SUMMARY OF THE INVENTION

It is an object of the present invention to remedy this drawback by providing an apparatus of particularly simple design which enables a predetermined quantity of pasty matter to be received and transferred, without the formation of air bubbles, into a hollow body such as syringe body.

To this end, this apparatus for transferring a pasty matter for filling a hollow body, such as a syringe body, is characterised in that it comprises a cylindrical bowl in which the pasty matter to be transferred is placed and of which the bottom is extended by an axial tube open at its two ends, a push member which may be engaged in the bowl to push the pasty matter towards and into the axial tube, this push member having an outer diameter substantially equal to the inner diameter of the bowl and having an axial bore passing therethrough, and a piston constituted by a rod of diameter equal to the inner diameter of the axial tube extending the bowl, housed and slidable in the axial bore of the push member to be engaged in the axial tube of the bowl and empty this tube of the pasty matter that it contains. The apparatus according to the invention offers the advantage that it may be completely emptied of the pasty matter that it contains due to the double-piston system that it comprises, the push member ensuring the emptying of the bowl whilst the rod forming the piston empties the axial tube extending from the bowl. Consequently, the apparatus according to the invention avoids any loss of pasty matter transferred in the hollow body.

The apparatus according to the invention also offers the advantage that, once placed upside down, the inner piston whose rod then projects axially above the push member, may constitute a vertical support on which the axial tube extending from the bowl may be engaged. This latter is then held in a perfectly horizontal position and it allows easy filling of the bowl to a determined level as a function of the quantity of pasty matter to be transferred, this level being locatable with respect to circles marked transversely on the side wall of the bowl made of transparent material.

BRIEF DESCRIPTION OF THE DRAWINGS

The invention will be more readily understood on reading the following description with reference to the accompanying drawings, in which:

FIG. 1 is a view in axial section of an apparatus for transferring pasty matter, the push member and its piston being shown out of the bowl.

FIG. 2 is a view in elevation, partly in vertical section, of the transfer apparatus in vertical position for filling the bowl;

FIG. 3 is a view in elevation of the push member and its piston separated from the bowl, after the latter has been filled.

FIG. 4 is a view in elevation of the push member and its piston after it has been turned over and is in abutment against a surface in order to cause the head of the rod forming piston to extend out of the push member.

FIG. 5 is a view in axial section of the apparatus in which the tube is engaged in a hollow body to be filled, in the course of the first phase of the transfer of the pasty matter during which the push member is progressively driven into the bowl.

FIG. 6 is a view in axial section similar to that of FIG. 5, in the course of the final phase of the transfer of the pasty matter during which the piston rod is progressively driven through the push member and into the axial tube extending from the bowl.

DESCRIPTION OF THE PREFERRED EMBODIMENT

Referring now to the drawings, the apparatus according to the invention essentially comprises three main constituent elements, namely a bowl 1 having a base 1a from which is extended an axial tube 2 open at its two ends, a push member 3 and a piston 4 constituted by a rod passing through the push member 3.

The cylindrical bowl 1 comprises a side wall 1b which is preferably transparent so that the level of the pasty matter to be transferred can be observed therethrough in the course of the filling of the bowl, as illustrated in FIG. 2. This transparent side wall 1b may be provided, at predetermined intervals, with transverse circles (not shown) constituting a filling graduation.

The push member 3, advantageously made of molded plastic material, comprises an inner end part 3a forming a piston head, of which the outer diameter corresponds to the inner diameter of the side wall 1b of the bowl 1. This inner head 3a acts as piston to drive into the tube 2 the pasty matter to be transferred, as will be seen hereinafter. At its outer end, the push member 3 comprises a head 3b, whose diameter is larger than the inner head 3a and which serves as support for the hand during the pasty matter driving stroke. The push member 3 is, furthermore, pierced with an axial bore 3b through which the piston 4 extends.

This piston 4 comprises a rod 4a whose diameter is equal to that of the axial bore 3c of the push member 3, this rod terminating at its outer end, in a head 4b which may be retracted into a housing 3d provided in the front face of the outer head 3b of the push member 3. The piston rod 4a bears in its left-hand end part, which is opposite its outer head 4b, a transverse annular O-ring 4c whose diameter is slightly greater than the inner diameter of the tube 2 and which is consequently intended to be tightly sealed against the inner wall of this tube.

With more particular reference to FIGS. 2 to 6, the manner will now be described in which the apparatus according to the invention is used for transferring into a hollow body 5, such as a syringe body, a predetermined quantity of pasty matter constituted by a silicone-catalyst mixture forming an impression material to be injected.

For the filling operation, the apparatus is placed in vertical position on a support 6, as shown in FIG. 2. In this position, the push member 3 rests on the support 6 by its outer, large diameter head 3b, the head 4b of the piston 4 is retracted in the housing 3d of the outer head 3b, and the piston rod 4a projects upwardly, with respect to the inner head 3a of the push member. The vertical tube 2 which extends the bowl 1 downwardly is fitted on this rod. Said bowl is thus in a horizontal position. The upper end of the piston rod 4a obturates the upper orifice of the tube 2, at the spot where the latter is connected to the bottom 1a of the bowl 1. The bowl 1 may then be filled with a silicone-catalyst mixture 7 up to a predetermined level corresponding to the quantity of impression material to be injected.

Once this level is reached, the push member 3-piston 4 assembly is separated from the bowl 1, by disengaging the piston rod 4a from the vertical tube 2. The pasty matter 7 contained in the bowl remains therein, slowly flowing downwardly in the tube 2, due to the high viscosity of the silicone-catalyst mixture.

The push member 3-piston 4 assembly is then turned over through 180° and the end of the piston rod 4a is supported on the support 6, so that it slides inside the push member 3 until it is completely pushed upwardly and the head 4b of the piston rod 4a is spaced apart to a maximum from the outer head 3b of the push member 3.

The silicone-catalyst mixture is then transferred into the body of the syringe 5, as is illustrated in FIGS. 5 and 6. To this end, the tube 2 of the bowl 1 is first introduced in the bottom of the hollow body 5, up to the plunger of the syringe. The push member 3 and more particularly its inner head 3a, is then engaged in the bowl 1 and a thrust is exerted on the outer head 3b of this push member, to cause the latter to penetrate progressively in the bowl 1. The push member 3 then pushes along the silicone-catalyst mixture which is forced into the tube and passes from there into the inside of the syringe body 5, progressively filling this body from the bottom. This progressive filling takes place without the formation of bubbles.

When all the matter contained in the bowl 1 has been pushed into the tube 2 and the syringe body 5, i.e. when the push member 3 is in its extreme left-hand as shown in FIG. 6, the tube 2 is emptied, during the second phase of the filling, by sliding the piston 4. To this end, a pressure is exerted on the piston head 4b, this causing the piston rod 4 to slide towards the left in FIG. 6, through the push member 3, at that time at the end of its stroke, and thus pushing along the silicone-catalyst mixture located in this tube. At the end of penetration stroke of the piston rod 4a, the whole of this mixture has been transferred inside the syringe body 5. There is no loss of silicone-catalyst mixture.

What I claim is:

1. Apparatus for transferring pasty matter without leaving a substantial amount of pasty material remaining in the apparatus comprising:
    a cylindrical bowl having an open top and a base closing a bottom of said bowl;
    a hollow tube axially joined to said base having a bore therein opening axially into said bottom;
    a push member;
    a head on said push member, said head being sealingly and slideably fittable through said open top into said cylindrical bowl;
    said head on said push member being effective when pushed into said cylindrical bowl to urge said pasty matter therein toward said base and into said bore in said hollow tube;
    an axial bore extending through said push member;
    said axial bore being axially aligned with said bore in said hollow tube when said head is fitted into said cylindrical bowl;
    a piston slideably fitted in said axial bore;
    said piston having a length substantially greater than a length of said axial bore; and
    said piston being sealingly slideable into said bore in said hollow tube and effective when forced thereinto to urge said pasty matter substantially completely through said hollow tube without leaving a substantial amount of said pasty material in said bore.

2. Apparatus according to claim 1, wherein said piston includes an O-ring effective for sealing in said hollow tube.

3. Apparatus according to claim 1, further comprising:
    a head at an outer end of said piston external to an end of said push member remote from said head; and
    a housing in said push member adapted for containing said head when said head is moved a substantial distance toward said head.

4. Apparatus according to claim 2, wherein said push member includes a surface at an end remote from said head, said surface being effective to support said push member on a horizontal surface with said head recessed in said housing and said piston extending substantially vertically upward.

5. Apparatus according to claim 4, wherein an end of said hollow tube remote from said base is fittable over said piston extending substantially vertically upward and effective to support said hollow tube and cylindrical bowl in an upright position.

6. Apparatus according to claim 5, wherein an end of said piston is substantially parallel to an inner surface of said base when said hollow tube and cylindrical bowl are supported thereon.

* * * * *